(12) United States Patent
Rouau et al.

(10) Patent No.: US 6,929,936 B1
(45) Date of Patent: Aug. 16, 2005

US006929936B1

(54) COMPOSITION COMPRISING AN ENZYME HAVING GALACTOSE OXIDASE ACTIVITY AND USE THEREOF

(75) Inventors: Xavier Rouau, Montpelier (FR); Mette Schrøder, Kolding (DK); Jørn Borch Søe, Mundelstrup (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/462,911

(22) PCT Filed: Jul. 16, 1998

(86) PCT No.: PCT/DK98/00335

§ 371 (c)(1),
(2), (4) Date: Feb. 15, 2000

(87) PCT Pub. No.: WO99/03351

PCT Pub. Date: Jan. 28, 1999

Related U.S. Application Data

(60) Provisional application No. 60/053,451, filed on Jul. 22, 1997.

(30) Foreign Application Priority Data

Jul. 18, 1997 (DK) .............................................. 0878/97

(51) Int. Cl.[7] ............................ C12N 9/04; A23L 11/05
(52) U.S. Cl. ...................................... 435/190; 426/653
(58) Field of Search .......................... 435/190; 426/653

(56) References Cited

U.S. PATENT DOCUMENTS

| | | | |
|---|---|---|---|
| 2,783,150 A | | 2/1957 | Luther |
| 3,832,340 A | * | 8/1974 | With et al. |
| 3,926,732 A | * | 12/1975 | Rosen et al. |
| 4,048,018 A | * | 9/1977 | Coughlin et al. |
| 4,344,968 A | * | 8/1982 | Aoda et al. |
| 4,458,686 A | * | 7/1984 | Clark, Jr. .................... 128/635 |
| 4,609,640 A | * | 9/1986 | Morishita et al. |
| 4,617,190 A | * | 10/1986 | Montgomery |
| 4,820,520 A | * | 4/1989 | Yokotsuka et al. ......... 424/439 |
| 4,828,853 A | * | 5/1989 | Banks et al. .................. 426/94 |
| 4,867,973 A | * | 9/1989 | Goers et al. |
| 5,063,072 A | * | 11/1991 | Gillmore et al. ............ 426/557 |
| 5,156,840 A | * | 10/1992 | Goers et al. |
| 5,478,576 A | * | 12/1995 | Jung et al. |
| 5,490,988 A | * | 2/1996 | Beggs et al. |
| 5,662,933 A | * | 9/1997 | Baichwal et al. |

FOREIGN PATENT DOCUMENTS

| | | |
|---|---|---|
| CA | 2012723 | 9/1990 |
| DE | 195 41 846 A1 | 5/1997 |
| WO | B1-321-811 | 6/1989 |
| WO | B1-338-452 | 10/1989 |
| WO | WO 93/25239 | * 12/1993 |
| WO | WO 94/28728 | 12/1994 |
| WO | WO 95/01727 | 1/1995 |
| WO | WO 95/29996 | 11/1995 |
| WO | WO 96/39851 | 12/1996 |

OTHER PUBLICATIONS van der Lugt et al., The First European Symposium on Enzymes and Grain Processing, Proceedings of ESEGP–1, Dec. 2–4, 1996, pp. 164–176.*

Somers et al., Cereal Foods World, Jul. 1996, vol. 41, No. 7, p. 550.*

* cited by examiner

*Primary Examiner*—Michael Meller
(74) *Attorney, Agent, or Firm*—Steptoe & Johnson LLP

(57) ABSTRACT

A dough and bread improving composition comprising an enzyme having galactose oxidase activity and an oxidizable substrate for this enzyme and/or an enzyme which is capable of converting a compound, e.g. a galactose-containing compound into a substrate for the enzyme having galactose oxidase activity.

19 Claims, 4 Drawing Sheets

Figure 1:
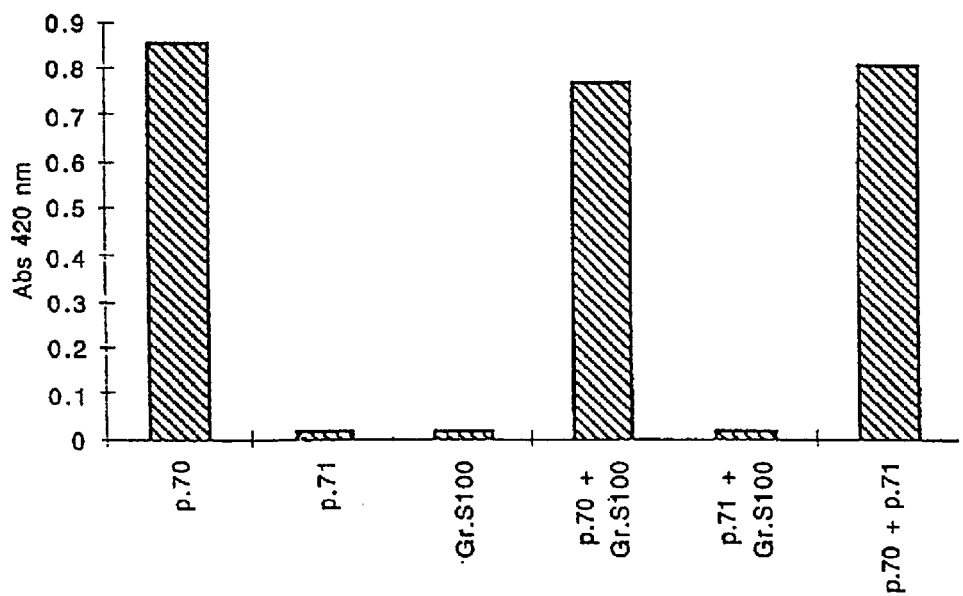

COMPOSITION COMPRISING AN ENZYME HAVING GALACTOSE OXIDASE ACTIVITY AND USE THEREOF

This application claims benefit of Ser. No. 60/053,451 dated Jul. 22, 1997

FIELD OF THE INVENTION

The present invention pertains to the field of improving the rheological characteristics of flour doughs and the quality of baked bread products.

TECHNICAL BACKGROUND AND PRIOR ART

In the baking industry it is an important objective to provide bread products which have a soft crumb structure, a high specific volume and which are not prone to staling within the desirable shelf life for fresh bread products.

One prerequisite for obtaining bread products having such a desired quality is the provision of a dough having appropriate rheological and structural characteristics. In this connection, the "strength" or "weakness" of doughs is an important aspect of making farinaceous finished products from doughs, including baking. The "strength" or "weakness" of a flour dough is primarily determined by the protein content of the flour and in particular, the content and the quality of the gluten protein is an important factor in that respect. Flours with a low protein content is generally characterized as "weak". Thus, the cohesive, extensible, rubbery mass which is formed by mixing water and weak flour will usually be highly extensible when subjected to stress, but it will not return to its original dimensions when the stress is removed.

Flours with a high protein content are generally characterized as "strong" flours and the mass formed by mixing such a flour and water will be less extensible than the mass formed from a weak flour, and stress which is applied during mixing will be restored without breakdown to a greater extent than is the case with a dough mass formed from a weak flour.

Strong flour is generally preferred in most baking contexts because of the superior rheological and handling properties of the dough and the superior form and texture qualities of the finished baked or dried products made from the strong flour dough.

Within the bakery and milling industries it is known to use dough "conditioners" to strengthen the dough. Such dough conditioners are normally non-specific oxidizing agents such as e.g. iodates, peroxides, ascorbic acid, K-bromate or azodicarbonamide and they are added to dough with the aims of improving the baking performance of flour to achieve a dough with improved stretchability and thus having a desirable strength and stability. The mechanism behind this effect of oxidizing agents is that the flour proteins, in particular gluten contains thiol groups which, when they become oxidized, form disulphide bonds whereby the protein forms a more stable matrix resulting in a better dough quality and improvements of the volume and crumb structure of the baked products.

However, the use of several of the currently available oxidizing agents is either objected to by consumers or is not permitted by regulatory bodies and accordingly, it has been attempted to find alternatives to these conventional flour and dough additives and the prior art has i.a. suggested the use of glucose oxidase for this purpose.

Thus, U.S. Pat. No. 2,783,150 discloses the addition of glucose oxidase to flour to improve dough strength and texture and appearance of baked bread. CA 2,012,723 discloses bread improving compositions comprising cellulolytic enzymes such as xylanases and glucose oxidase, the latter enzyme being added to reduce certain disadvantageous effects of the cellulolytic enzymes (reduced dough strength and stickiness) and it is disclosed that addition of glucose to the dough is required to obtain a sufficient glucose oxidase activity.

EP-B1-321 811 discloses the use of an enzyme composition comprising glucose oxidase and sulfhydryl oxidase in combination to improve the rheological characteristics of doughs. It is mentioned in this prior art document that the use of glucose oxidase alone has not been successful.

In EP-B1-338 452 is disclosed an enzyme composition for improving dough stability, comprising a mixture of cellulase/hemicellulase, glucose oxidase and optionally sulfhydryl oxidase.

However, the use of glucose oxidase as a dough improving additive has the limitation that this enzyme requires the presence of sufficient amounts of glucose as substrate in order to be effective in a dough system and generally, the glucose content in cereal flours is low. Therefore, the absence of glucose in doughs or the low content hereof in doughs will be a limiting factor for the effectiveness of glucose oxidase as a dough improving agent. Thus, it may be required to add sucrose or glucose as substrate to the dough to obtain a sufficient effect and glucose oxidase does not constantly provide a desired dough or bread improving effect when used alone without the addition of other enzymes.

Recently, it has been suggested to use hexose oxidase for improving the quality of flour dough (WO 96/39851).

Cellulases and/or hemicellulases (hemicellulases are also referred to herein as pentosanases or xylanases) which cleave non-starch polysaccharides contained in flour are used as a means of improving bread quality. The cleavage of glycosidic bonds in the non-starch polysaccharides affects the water retention and water binding capacity, viscosity and proofing capacity of the dough as well as the texture, aroma, taste and freshness of the bread. Generally speaking, the use of cellulases/hemicellulases gives an improved oven spring to the dough and an improved bread volume, grain structure and anti-staling properties to the finished bakery product.

However, the use of cellulases or hemicellulases involve certain undesirable side effects. In particular, it is commonly observed that the addition of these enzymes to doughs results in that the doughs become too slack and sticky, which may cause problems. It is therefore necessary to use dosages of cellulases or hemicellulases which are too low for an optimum baking result to be achieved, so that the enzymes in question cannot be utilized to the full extent. At low dosage level, cellulases or hemicellulases make the mechanical handling of the dough easier whereas the effect of such enzymes on the process tolerance (dough stability) may be insufficient when used alone and accordingly, emulsifiers have to be used as additives.

It has now been found that the above problems associated with the use of cellulases or hemicellulases in flour doughs can be reduced or prevented by using these enzymes in combination with an oxidoreductase such as galactose oxidase under conditions where sufficient substrate for the latter enzyme is present in the dough. Therefore, by using such a combination of enzymes it has become possible to achieve the maximum effect of cellulases or hemicellulases, including the use of these enzymes in high amounts in doughs without the occurrence of stickiness and/or slackness herein.

Being an oxidoreductase, galactose oxidase will, in addition to the above effects, provide the dough strengthening effect and thereby improve the rheological characteristics of flour doughs as a result of formation of disulphide bonds in S-containing amino acids and also, as it was demonstrated by the inventors, as the result of binding ferulic acid binding to other ferulic acid moieties.

Galactose oxidase (D-galactose:oxygen 6-oxidoreductase, EC 1.1.3.9) is an enzyme which in the presence of oxygen is capable of oxidizing galactose to the corresponding lactone, D-galacto-hexodialdose with subsequent hydrolysis to the aldobionic acid. Accordingly, the oxidation catalyzed by galactose can be illustrated as follows:

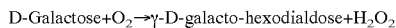

D-Galactose+$O_2$→γ-D-galacto-hexodialdose+$H_2O_2$

However, the natural content of galactose or other oxidizable substrates for galactose oxidase in cereal flours is very low, typically in the range of 0.001 to 0.01 wt %. Practical use of that enzyme in a flour based dough is therefore not possible without providing in the dough a sufficient amount of oxidizable substrates for the enzyme.

SUMMARY OF THE INVENTION

Accordingly, the invention relates in a first aspect to a composition comprising as a first component an enzyme having agalactose oxidase activity and as a second component an oxidizable substrate for the enzyme having galactose oxidase activity and/or an enzyme which is capable of converting a galactose-containing compound into a substrate for the enzyme having galactose oxidase activity.

In further aspects, the invention pertains to a method of preparing a flour dough comprising adding to the dough an amount of the above composition which is sufficient to obtain an amount of an enzyme having galactose oxidase activity in the dough which is in the range of 1 to 10,000 units per kg of flour, and a method of preparing a bakery product, comprising baking such a flour dough.

In yet a further aspect, the invention relates to the use of the above compositions as dough and/or bread improving agents.

DETAILED DISCLOSURE OF THE INVENTION

In accordance with the invention, any such enzyme which under dough conditions is capable of oxidizing a substrate naturally present in the dough or being generated in the dough is encompassed by the scope of the invention.

A presently preferred oxidoreductase is an enzyme having galactose oxidase activity including the above D-galactose:oxygen 6-oxidoreductase, EC 1.1.3.9 and other oxidoreductases which in the presence of oxygen are capable of oxidizing D-galactose. Such enzymes include e.g. hexose oxidase (EC 1.1.3.5), L-Sorbose oxidase (EC 1.1.3.11). Such other oxidoreductases are encompassed by the invention.

A suitable enzyme having galactose oxidase activity can be derived from any natural source including a plant, a prokaryotic organism such as a bacterial species, a eucaryotic organism such as a fungal species, including a yeast species and a species of filamentous fungi. Other possible sources are animal tissues.

It is well-known that crude ferments e.g. of filamentous fungi contain a multiplicity of enzyme activities. It is possible that such crude enzyme preparations may contain galactose oxidase activity, and they may therefore serve as sources of an least partially purified galactose oxidase preparation. In this connection it is contemplated that specific species of organisms can be selected which have a particularly high production of galactose oxidase. Such selected strains may be improved with respect to their production of galactose oxidase by any conventional strain improvement method, e.g. using random mutagenesis or site-directed mutagenesis.

The natural content of immediately oxidizable substrates for a galactose oxidase active enzyme is, as it is mentioned above, so low in cereal flours that any significant oxidizing effect of galactose oxidase in a flour dough cannot be expected unless there is provided in the composition of the invention or in the dough an appropriate amount of oxidizable substrate for the galactose oxidase or an extremely high amount of galactose oxidase is added.

In accordance with the invention, the composition therefore contains an oxidizable substrate for the galactose oxidase and/or an enzyme which is capable of converting a galactose-containing compound into a substrate for the galactose oxidase.

Although D-galactose as free molecules is the obvious oxidizable substrate for an oxidoreductase having galactose oxidase activity, useful substrates for the enzyme include any galactose-containing compound, in which galactose moieties are present in a position and a configuration where they can be oxidized by galactose oxidase.

Cereal flour has a natural content of non-starch polysaccharides comprising galactose moieties as structural elements, in particular hemicellulose compounds, including compounds which are generally referred in the art as pentosans or xylans. It was found that such structural components hereof are useful substrates for galactose oxidase.

One such useful substrate for galactose oxidase is a hydrolysis product of arabinogalactan, which is a component of the water soluble pentosans naturally present in cereal flours. Arabinogalactan derived from wheat and other cereal grains, such as rye, barley, rice, millet and oat is a glycoprotein consisting predominantly of a galactose- and arabinose-containing polysaccharide and a protein. In flour the content of arabinogalactan glycoprotein is typically in the range of 0.2–0.4 wt %.

Arabinogalactans are highly branched structures in which galactose residues are glycosidically bonded to each other with β-(1->3)-and β(1->6)-linkages to form galactan chains. Single arabinose units are bonded β-glycosidically to the galactan chains. The complete depolymerisation of arabinogalactan requires the steps of cleaving arabinose from the galactan chain by means of an arabinofuranosidase, hydrolysing β-(1->3)- and β(1->6)-linkages by means of galactanases to obtain oligomeric or dimeric galactose residues and finally releasing single galactose units by reacting the oligomers or dimers with a β-galactosidase.

In accordance with the invention, any of the above end products from hydrolysis of arabinogalactans has been shown to be suitable substrates for galactose oxidase. Particularly, it was surprisingly found that galactose moieties when present in a galactan is significantly more accessible to oxidation by the galactose oxidase than are galactose monomers.

In suitable embodiments, the galactose oxidase-containing composition according to the invention therefore includes a substrate compound which is selected from the group consisting of a galactan, a galactose oligomer or dimer, or galactose.

It is also contemplated that lactose, which e.g. can be incorporated in a flour dough in the form of milk powder, can be used as a substrate compound for galactose oxidase.

In certain preferred embodiments of the invention, the galactose oxidase-containing composition comprises as a second component an enzyme which is capable of converting a galactose-containing compound which is not in itself a substrate for the galactose oxidase into a substrate for the galactose oxidase. The galactose-containing compound to be converted may also be a compound which can act as a substrate for the galactose oxidase, but which by being treated with a second component enzyme is converted to a product which is more readily oxidized by galactose oxidase.

Thus, the formation of an oxidizable substrate in the dough for the galactose oxidase by such a second component enzyme would result in the following reactions:

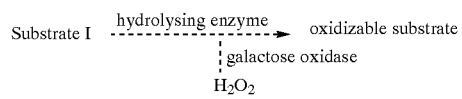

Such a convertible galactose-containing compound (substrate I) can either be a compound which is naturally present in cereal flour in an amount which, by the enzymatic activity of the above second component hydrolysing enzyme, is sufficient to provide the required oxidizable substrate for the galactose oxidase or a component hereof, or, if such a substrate compound is not present in sufficient amount in the flour, it can be added to the composition of the invention in the required amount.

The galactose-containing substrate compound may be one which is not naturally present in cereal flours such as e.g. a gum including guar gum and locust bean gum. However, it is a significant aspect of the invention that the substrate compound for the second component enzyme can be a galactose-containing compound naturally present in cereal flour such as compounds which are generally referred to as hemicellulose, pentosans or xylans.

In accordance with the invention, a suitable second component enzyme is an enzyme which can hydrolyse or otherwise degrade galactose-containing compounds or structural components hereof to provide an oxidizable substrate for galactose oxidase. In this connection, particularly useful enzymes include a hemicellulase, a pentosanase, a xylanase, an arabinofuranosidase, a galactanase, a mannanase and a β-galactosidase.

In accordance with the invention, the galactose oxidase-containing composition may comprise further components which are conventionally used in dough or bread improver compositions. Such further components include e.g. further enzyme components such as cellulases, starch degrading enzyme, including amylases and pullulanases, lipases, proteases and oxidoreductases other than galactose oxidase, and conventional non-enzimic dough additive compound including as examples leavening agents, emulsifiers, preserving agents, oxidizing agents such as e.g. iodates, peroxides, ascorbic acid, K-bromate or azodicarbonamide.

It is an interesting aspect of the invention that the amount and the type of the second component of the composition can be selected so as to obtain any specifically desirable level of activity of the oxidoreductase.

The composition of the invention is suitably provided with an amount of galactose oxidase which is in the range of 1 to 10,000 units (Sigma) pr g, one Sigma unit being defined as the amount of galactose oxidase which will produce a $\Delta A_{425}$ of 1.0 per minute at pH 6.0 at 25° C. in a peroxidase and o-tolidine system, reaction volume of 3.4 ml and light passage of 1 cm (G. Avigad et al., J. Biol. Chem. 237:2736, 1962). In useful embodiments, the amount of galactose oxidase is in the range of 100 to 5,000 units per g, such as 500 to 4,000 units.

For certain applications, it is desirable to provide the galactose oxidase in a substantially pure form e.g. as a preparation essentially without other proteins or non-protein contaminants and accordingly, a relatively crude enzyme preparation resulting from a conventional procedure of extracting and isolating the enzyme from a source organism may be subjected to further purification steps such as further chromatography steps, gel filtration or chromatofocusing.

In further aspects, the invention pertains to a method of preparing a flour dough comprising adding to the dough an amount of the above composition which is sufficient to obtain an amount of galactose oxidase in the dough which is in the range of 1 to 10,000 units per kg of flour and a method of preparing a bakery product, comprising baking such a flour dough.

In a preferred embodiment of the method according to the invention, a flour dough is prepared by mixing flour with water, a leavening agent such as yeast or a conventional chemical leavening agent, and an effective amount of galactose oxidase-containing composition under dough forming conditions. It is, however, within the scope of the invention that further components can be added to the dough mixture.

Typically, such further dough components include conventionally used dough components such as salt, a sweetening agent such as sugars, syrups or artificial sweetening agents, lipid substances including shortening, margarine, butter or an animal or vegetable oil and one or more conventional dough additives such as emulsifying agents, starch degrading enzymes, cellulose degrading enzymes, proteases, lipases, non-specific oxidizing agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fiber substances.

Conventional emulsifiers used in making flour dough products include as examples monoglycerides, diacetyl tartaric acid esters of mono- and diglycerides of fatty acids, and lecithins e.g. obtained from soya. Among starch degrading enzymes, amylases are particularly useful as dough improving additives. α-amylase breaks down starch into dextrins which are further broken down by β-amylase into maltose. Other useful starch degrading enzymes which may be added to a dough composition include glucoamylases and pullulanases. In the present context, further interesting enzymes are xylanases and other oxidoreductases such as hexose oxidase, glucose oxidase, pyranose oxidase and sulfhydryl oxidase.

One preferred flour is wheat flour, but doughs comprising flour derived from other cereal species such as from rice, maize, barley, rye and durra are also contemplated.

The dough is prepared by admixing flour, water, the oxidoreductase according to the invention and other possible ingredients and additives. The composition according to the invention can be added together with any dough ingredient including the water or dough ingredient mixture or with any additive or additive mixture. The dough can be prepared by any conventional dough preparation method common in the baking industry or in any other industry making flour dough based products.

The amount of the composition added normally is an amount which results in the presence in the finished dough of 1 to 10,000 units of galactose oxidase per kg of flour, preferably 5 to 5000 units such as 10 to 1000 units. In useful embodiments, the amount is in the range of 20 to 500 units per kg of flour.

The effect of the galactose oxidase on the rheological properties of the dough can be measured by standard methods according to the International Association of Cereal Chemistry (ICC) and the American Association of Cereal Chemistry (AACC) including the amylograph method (ICC 126), the farinograph method (AACC 54-21) and the extensigraph method (AACC 54-10). The extensigraph method measures e.g. the doughs ability to retain gas evolved by yeast and the ability to withstand proofing. In effect, the extensigraph method measures the relative strength of a dough. A strong dough exhibits a higher and, in some cases, a longer extensigraph curve than does a weak dough. AACC method 54-10 defines the extensigraph in the following manner: "the extensigraph records a load-extension curve for a test piece of dough until it breaks. Characteristics of load-extension curves or extensigrams are used to assess general quality of flour and its responses to improving agents".

In a preferred embodiment of the method according to the invention, the resistance to extension of the dough in terms of the ratio between the resistance to extension (height of curve, B) and the extensibility (length of curve, C), i.e. the B/C ratio as measured by the AACC method 54-10 is increased by at least 10% relative to that of an otherwise similar dough not containing galactose oxidase. In more preferred embodiments, the resistance to extension is increased by at least 20%, such as at least 50 and in particular by at least 100%.

The method according to the invention can be used for any type of flour dough with the aims of improving the rheological properties hereof and the quality of the finished products made from the particular type of dough. Thus, the method is highly suitable for the making of conventional types of yeast leavened bread products including wheat flour based bread products such as loaves and rolls. However, it is contemplated that the method also can improve the properties of doughs in which leavening is caused by the addition of chemical leavening agents, including sweet bakery products such as cake products including as examples pound cakes and muffins, or scones.

In one interesting aspect, the method of the invention is used to improve the rheological properties of doughs intended for noodle products including "white noodles" and "chinese noodles" and to improve the textural qualities of the finished noodle products. A typical basic recipe for the manufacturing of noodles comprises the following ingredients: wheat flour 100 parts, salt 0.5 parts and water 33 parts. The noodles are typically prepared by mixing the ingredients in an appropriate mixing apparatus followed by rolling out the noodle dough using an appropriate noodle machine to form the noodle strings which are subsequently air dried.

The quality of the finished noodles is assessed i.a. by their colour, cooking quality and texture. The noodles should cook as quickly as possible, remain firm after cooking and should preferably not loose any solids to the cooking water. On serving the noodles should preferably have a smooth and firm surface not showing stickiness and provide a firm "bite" and a good mouthfeel. Furthermore, it is important that the noodles have a light colour.

Since the appropriateness of wheat flour for providing noodles having the desired textural and eating qualities may vary according to the year and the growth area, it is usual to add noodle improvers to the dough in order to compensate for sub-optimal quality of the flour. Typically, such improvers will comprise dietary fiber substances, vegetable proteins, emulsifiers and hydrocolloids such as e.g. alginates, carrageenans, pectins, vegetable gums including guar gum and locust bean gum, and amylases.

It is therefore an important aspect of the invention that the galactose oxidase-containing composition according to the invention is useful as a noodle improving agent, optionally in combination with other components currently used to improve the quality of noodles. Thus, it is contemplated that noodles prepared in accordance with the above method will have improved properties with respect to colour, cooking and eating qualities including a firm, elastic and non-sticky texture and consistency.

In a further useful embodiment the dough which is prepared by the method according to the invention is a dough for preparing an alimentary paste product. Such products which include as examples spaghetti and maccaroni are typically prepared from a dough comprising as the main ingredients flour such as e.g. Semolina, water and/or and eggs. After mixing of the ingredient, the dough is formed to the desired type of paste product and air dried. It is contemplated that the addition to a paste dough will have a significant improving effect on the extensibility and stability hereof resulting in a finished paste product having improved textural and eating qualities.

In a still further aspect, the invention relates to the use of a galactose oxidase as a dough and/or bread improving agent. In specific embodiments, such use include that the galactose oxidase is added to the dough ingredients, dough additives or the dough in the form of a preparation substantially not containing other enzyme activities, i.e. as a at least partially purified preparation, e.g. based on a crude enzyme extract or a fermentation medium in which a galactose oxidase producing organism has been cultivated. For certain purposes where it is not required to use such a purified enzyme preparation, the galactose oxidase can be provided in the form of a crude enzyme preparation.

Figure 2:
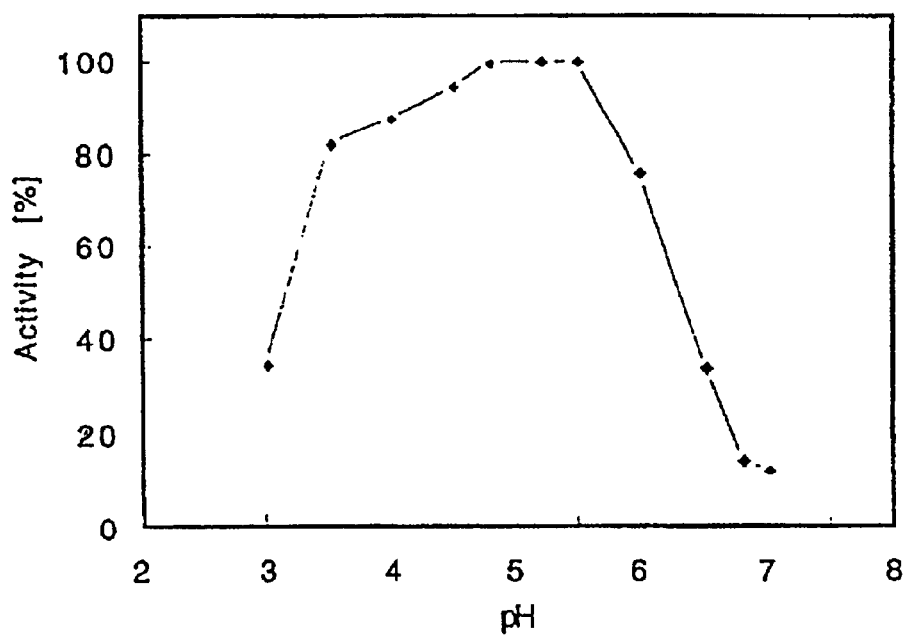
Figure 3:
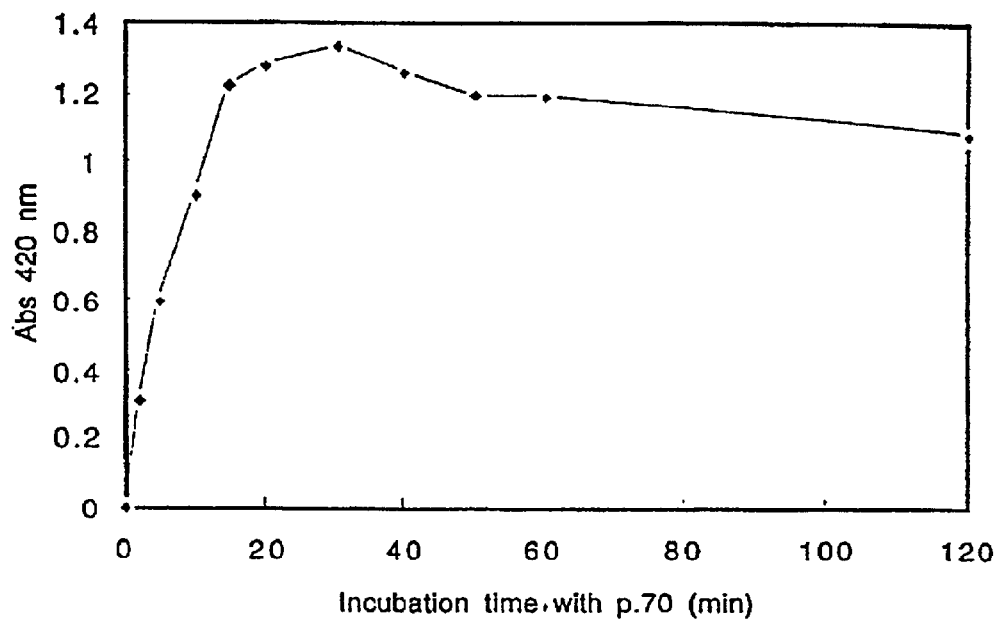
Figure 4:
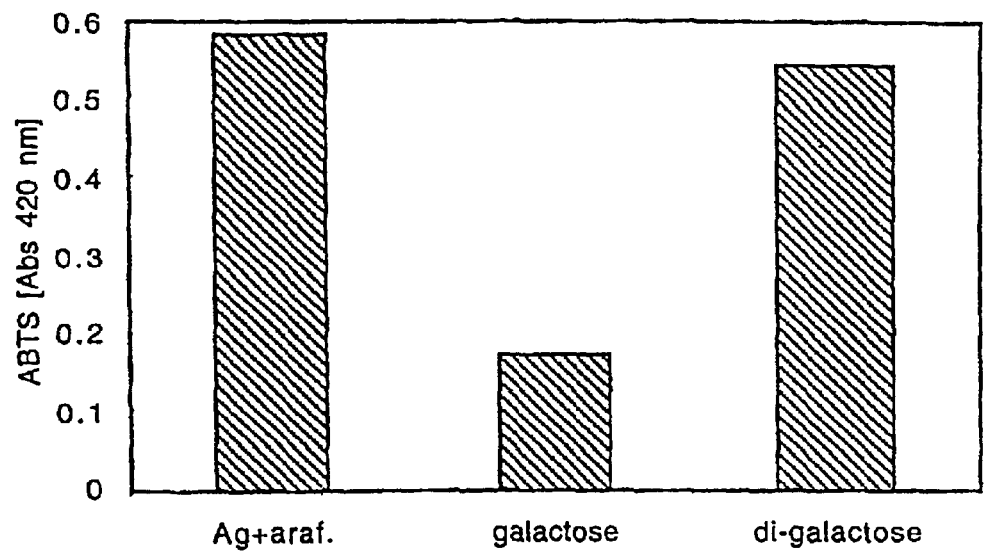

The invention is further illustrated by the following, nonlimiting examples and by the drawing wherein FIG. 1 illustrates oxidation of 2,2'-azino-bis(3-ethylbenzthiazoline-6-sulfonic acid) (ABTS) in a reaction mixture containing ABTS, galactose oxidase, arabinogalactan and one of the enzyme preparations: (i) Pectolytic enzyme 2524-70 (P70), (ii) Pectolytic enzyme 2524-71 (P71) and (iii). Grindamyl S 100, respectively (10 mg/ml), FIG. 2 shows the pH dependency of the reaction between arabinogalactan and the crude *Aspergillus* enzyme preparation P70, FIG. 3 illustrates the rate of generation of oxidizable substrate for galactose oxidase from arabinogalactan reacted with the crude enzyme preparation P70, determined by the ABTS assay, and FIG. 4 illustrates the oxidation by galactose oxidase of the following galactose-containing substrate: (i) galactose, (ii) di-galactose and (iii) arabinogalactan (5 mg/ml) treated with 300 µl of arabinofuranosidase (64 U/ml).

EXAMPLE 1

A water soluble preparation of pentosans (WSP) was isolated from Thesee flour as described by Faurot et al., Lebensm.-Wiss. u-Technol. 28:436–444, 1995.

The WSP preparation was used as the source for isolating arabinogalactan, which in turn was used as substrate to determine the oxidizing activity of galactose oxidase. The WSP preparation can also be used as a source of arabinoxylan.

1.1. Purification of Arabinogalactan from Water Soluble Pentosans.

Reagents

Amyloglycosidase solution: 10 mg/ml amyloglycosidase (101332, Merck) was dissolved in 0.01 M acetate buffer, pH 5.0.

Pronase solution: 10 mg/ml pronase (165921, Boehringer Mannheim) was dissolved in 0.5 M phosphate buffer, pH 7.5.

Procedure 25 g WSP (Theses flour) was added to 880 ml Millipore water and pH was adjusted to 5.5. The resulting solution was stirred overnight. 10 ml of amyloglucosidase solution was added and the enzyme reaction was allowed to proceed for 2 hours at 40° C. under stirring. The pH was adjusted to 7.5 by addition of 100 ml phosphate buffer. Subsequently, 10 ml pronase solution was added and the resulting mixture was incubated at 40° C. for 2 hours. The mixture was heated to 95° C. and kept at this temperature for 10 minutes to inactivate the pronase. Subsequently, the mixture was cooled to room temperature and centrifuged for 30 minutes at 4° C. (12,000×g). The resulting supernatant was adjusted with 96% ethanol to obtain a pentosan solution at a concentration of 60% (v/v) ethanol.

Precipitation of Arabinoxylan.

The above obtained pentosan solution was submitted to precipitation for 1 hour at 4° C., the precipitate was washed twice with 60% ethanol on a glass filter (No. 2) using vacuum without drying the precipitate totally. Subsequent washings of the precipitate with 96% ethanol, absolute ethanol and finally with acetone resulted in a precipitate of arabinoxylan which was dried at 35° C. overnight.

Isolation of Arabinogalactan.

The supernatant obtained after the above precipitation of arabinoxylan was adjusted to 80% ethanol and subjected to precipitation of arabinogalactan. The precipitate was dissolved in Millipore water (2% w/v), precipitated in 80% ethanol, the supernatant was discarded and the precipitate was centrifuged at 12,000×g for 30 minutes at 4° C. The resulting pellet was dissolved in Millipore water and freeze-dried.

1.2. The Generation of Oxidizable Substrates for Galactose Oxidase from Arabinogalactan The generation of oxidizable substrates from arabinogalactan was tested by treating the above arabinogalactan solution with 3 different enzyme preparations.

The ability of the resulting enzyme treated solutions to act as substrate by galactose oxidane resulting in production of $H_2O_2$ was tested using ABTS. Oxidation of ABTS by the produced $H_2O_2$ will, in the presence of a peroxidase, lead to the formation of a coloured compound which can be detected by measuring the optical density (OD) of the reaction mixtures at 420 nm.

250 µl of the above precipitated arabinogalactan dissolved in 0.1 M Na-acetate buffer (20 mg/ml), pH 5.0, was incubated at room temperature for 90 minutes with 5 µl of the following enzyme preparations:

(i) Pectolytic enzyme 2524-70 (P70) (10 mg/ml), Danisco Ingredients. This preparation is a crude ferment of *Aspergillus niger* containing several enzyme activities such as pectolytic activity, (ii) Pectolytic enzyme 2524-71 (P71) (10 mg/ml), Danisco Ingredients. This preparation is also a crude ferment of *Aspergillus niger* containing several enzyme activities such as pectolytic activity, and (iii) Grindamyl S 100 (10 mg/ml), Danisco Ingredients. This commercial enzyme product is also a crude ferment of *Aspergillus niger* which is used mainly as a source of amylase and xylanase activities.

The enzymatic reactions were terminated by boiling for 5 minutes. The samples were centrifuged at 12,000×g and the supernatants were used for further testing with the ABTS assay.

1.2.1. ABTS Assay

ABTS assay reaction mixture: 6.25 mg ABTS (Sigma A-1888) dissolved in 10 ml 0.1 M Na-phosphate buffer, pH 6.4 is mixed with 160 µl galactose oxidase (30 units/ml) (Sigma G-7400) and 160 µl peroxidase (200 U/ml) (Sigma P-8124). 0.1 M Naphosphate buffer, pH 6.4, is added ad 25 ml.

The ABTS reaction mixture is incubated with a potential substrate for galactose oxidase to be tested and the absorbance at 420 nm is read immediately.

1.2.2. The Effect of Treating Arabinogalactan with the Above Enzyme Preparations (i), (ii) and (iii) on the Generation of Oxidizable Substrates for Galactose Oxidase 800 µl ABTS reaction mixture was incubated with 50 µl enzyme-treated arabinogalactan solution in cuvettes for 30 minutes at room temperature. The absorbance at 420 nm was read immediately. The results are shown in FIG. 1. It can be seen that when arabinogalactan was treated with the P70 preparation it resulted in the formation of oxidizable substrates for galactose oxidase whereas the treatment with P71 and Grindamyl S 100 did not result in the formation of oxidizable substrates at pH 5.0. Experiments performed with P71 at pH 3.0, however, did result in oxidizable substrates for galactose oxidase.

1.2.3. The Effect of pH on the Generation of Oxidizable Substrates for Galactose Oxidase from P70 Treated Arabinogalactan 800 µl ABTS reaction mixture was incubated at pH values in the range of 3 to 7 with 50 µl enzyme-treated arabinogalactan solution in cuvettes for 30 minutes at room temperature. The absorbance at 420 nm was read immediately. The results are shown in FIG. 2. It appears that high levels of oxidizable substrates were generated at pH values in the range of 3.5 to 6, with a pH optimum about 5. At pH 3 only 34% of the maximum activity was detected and at pH 7 an activity of only 12% of the maximum activity was obtained.

1.2.4. The Effect of Incubation Time on the Generation of Oxidizable Substrate for Galactose Oxidase by P70

300 µl arabinogalactan (20 mg/ml) was incubated with 5 µl P70 and the enzyme reaction was stopped at different time intervals. The generation of oxidizable substrates for galactose oxidase was detected using the ABTS assay. The results are shown i FIG. 3. From the figure it is evident, that the rate of generation of oxidizable substrate was particularly high during the first 15 minutes. After 30 minutes of reaction there was a maximum level of galactose oxidase oxidation. Increasing the reaction time further did not increase the release of oxidizable substrates further.

1.2.5. Identification of Arabinogalactan Degrading Enzyme Activities Present in P70

P70 was fractionated by hydrophobic interaction chromatography (HIC) and the fractions were screened for several enzymatic activities.

p-nitrophenyl β-D-galactopyranoside (pNPG) and p-nitrophenyl 6-O-β-D-galactopyranosyl-β-D-galactopyranoside (pNPGG) were used as substrates to detect β-galactosidase and 1->6-galactanase activities, detecting respectively enzymes releasing single galactose units and enzymes capable of releasing the 1->6 bound galactose dimer from a paranitrophenol unit. The fractions were also screened for arabinofuranosidase activity using p-nitrophenyl α-L-arabinofuranoside (pNPA) and for endo-xylanase activity.

Galactosidase activity was detected in two peaks around fraction 10 and fraction 17, whereas 1->6 galactanase activity represented a single peak (fractions 8 and 9). Released reducing sugars followed arabinofuranosidase activity, mainly in fractions 8 and 9.

The release of arabinose and di-galactose from arabinogalactan corresponded to activities measured on p-nitrophenyl substrates, maximum arabinose was released in fraction 8, whereas di-galactose had a maximum around fraction 9. The release of galactose was only observed in fractions 8 and 9. Thus fractions 8 and 9 contained arabinofuranosidase, activities releasing di-galactose and activities releasing galactose units.

Endo-xylanase activity was found in fractions 12 and 13.

EXAMPLE 2

Oxidation of Galactose-containing Compounds by Galactose Oxidase

Three different galactose-containing compounds were compared as substrates for galactose oxidase: (i) arabinogalactan treated with arabinofuranosidase, i.e. arabinogalactan with arabinose cleaved off, (ii) galactose and (iii) di-galactose. (FIG. 4). It can be seen that arabinose-free arabinogalactan was the most favourable of the tested substrates when compared on a galactose oxidase equivalent basis. Digalactose was oxidized nearly as good, but galactose was about three times less effective as substrate for galactose oxidase as compared to arabinofuranosidase treated arabinogalactan.

EXAMPLE 3

The Effect of Galactose Oxidase on Flour in a Model Dough System 3.1. Obtaining Purified Galactose Oxidase from a Crude Galactose Oxidase Preparation A commercially available galactose oxidase preparation is the crude ferment of the enzyme from Sigma, catalogue No. G7400.

This preparation contains a mixture of enzyme activities and it was purified to ensure that any oxidative effect obtained was solely a result of galactose oxidase activity. G7400 is provided as an amount of lyophilized powder of a crude enzyme preparation containing a declared activity of 10,000 Sigma units. The preparation was purified in the following 3 steps:

1) The 10,000 units of galactose oxidase was dissolved in 60 ml of water and filtered through a GP/B filter and subsequently through a 0.45 μm filter. This filtrate was applied to a 550 ml Sephadex G25 C desalting column (XK50, 5×28.5 cm). The column was equilibrated in 20 mM triethanolamine (TEA) buffer, pH 7.3 and eluted at a flow rate of 15 ml/minute.
2) The eluate resulting from the above step was applied to a column with 20 ml Q-sepharose 15 (XK16) equilibrated in 20 mM triethanolamine, pH 7.3. The column was washed with the equilibration buffer and the bound proteins eluted using 1 M NaCl in equilibration buffer. The column was eluted at a rate of 5 ml/minute. Fractions containing galactose oxidase activity were collected and pooled.
3) The above pooled sample was further purified by hydrophobic interaction chromatography applying the sample to a 20 ml Source Q15 column (XK16). The column was washed with 1 M ammonium sulphate in 20 mM Na-acetate, pH 5.0. The column was eluted using 20 mM Na-acetate, pH 5.0 at a rate of 5 ml/minute. Fractions containing galactose oxidase activity as determined by the below assay, were collected and pooled.

Galacotse oxidase activity was determined by an agarose plate assay according to the following procedure:
(i) A substrate solution was prepared by mixing 3.4 g of D-galactose and 44.4 mg of ABTS in a 100 volumetric flask followed by adding 60 ml of 0.1 M degassed Na-acetate buffer, pH 5.6, 1 ml of peroxidase solution and 0.0088 g of L-ascorbic acid. Additional buffer was added to 100 ml.
(ii) An agarose solution was prepared by dissolving 2 g of agarose in 100 ml of the above buffer at 70° C.
(iii) Equal volumes of the substrate solution (pre-heated to 70° C.) and the heated agarose solution was combined and poured into petri dishes. After solidifying, wells were made in the substrate/agarose medium which were loaded with fraction samples. The plates were incubated at 40° C. and the presence of galactose oxidase activity in a sample was detected by the occurrence of a dark green zone aroud the loaded wells.

The eluted protein was subjected to SDS-PAGE and silver stained and based on the fact that only one visible band at about 75 kDa in the gel was found it was concluded that the crude preparation had been purified to only contain galactose oxidase. The purified galactose oxidase was labelled with 2524-122-2 and the labelled enzyme preparation contained 69.4 units per ml.

3.2. The Effect of Purified Galactose Oxidase on Crosslinking Between Thiol Groups in a Wheat Flour Model Dough System The effect of the above purified galactose oxidase alone and in combination with P70 (Pectolytic enzyme 2524-70, Danisco Ingredients) on the formation of thiol group crosslinking was studied by measuring the content of free thiol groups in a model dough system.

3.2.1. Reagents
(i) 0.558 g of EDTA and 12.114 g TRIS is dissolved in distilled water ad 500 ml. pH was adjusted to 8.0 with HCl;
(ii) 0.396 g of 5,5'-dithio-bis(2-nitrobenzoic acid) (DTNB) was dissolved in reagent (i) ad 50 ml. This reagent is sensitive to day light and was kept in flasks covered with aluminium foil.

3.2.2. Procedure

The model dough was prepared in 15 ml Wheaton tubes from 1 g of Corde Noir flour and 20 mg NaCl to which was added 0, 3,470 and 5,205 units of purified galactose oxidase per kg flour respectively in combination with 0, 2,500 and 5,000 ppm, respectively of P70, and water ad 3 ml. A blank without flour and enzyme was also analyzed. The mixtures were agitated for 10 minutes.

Subsequently, 5 ml of reagent (ii) was added and the tubes were covered to prevent exposure to day light and agitation was continued for 10 minutes. 2 ml of the resulting reaction mixture was transferred to a 3 ml centrifugation tube and centrifuged at 10,000×g for 10 minutes. 0.100 ml aliquots of the resulting supernatant were transferred to Elisa plates and OD at 420 nm was measured.

The measurement was carried out essentially in accordance with the calorimetric method of Ellman (1958) as also described in Cereal Chemistry, 1983, 70, 22–26. This method is based on the principle that DTNB reacts with thiol groups in the dough to form a highly coloured anion of 2-nitro-5-mercapto-benzoic acid, which is measured using a spectrophotometer at 420 nm.

3.2.3. Results

Assuming that the relative change of the amount of thiol groups in a dough is reflected as the change in the optical density (OD) resulting from the reaction between thiol groups and DTNB in the dough, the following results (average of two determinations) were obtained:

| Pectolase 2524-70 ppm | Galactose oxidase 2524-122-2 U/kg flour | Thiol µmol/g flour |
|---|---|---|
| 0 | 0 | 0.714 |
| 2500 | 0 | 0.657 |
| 5000 | 0 | 0.650 |
| 0 | 3470 | 0.433 |
| 2500 | 3470 | 0.407 |
| 5000 | 3470 | 0.313 |
| 0 | 5205 | 0.213 |
| 2500 | 5205 | −0.068 |
| 5000 | 5205 | −0.071 |

Thus, this experiment showed a significant decrease in the content of free thiol groups which was proportionate to the amount of galactose oxidase added. When P70 was added the decrease in the content of free thiol groups was significantly higher at a lower concentration of galactose activity, indicating that there is an interactive effect between P70 and galactose oxidase.

EXAMPLE 4

4.1. Improvement of the Specific Volume of Bread by Adding Galactose Oxidase and P70 to the Dough Doughs were prepared from 40 g flour, 300 mg lyophilised yeast, 20 ml 4.4% NaCl. Enzyme solutions (see table 4.1) were added hereto. A dough prepared without added enzyme solution served as a control. The doughs were mixed for 5 minutes followed by resting for 5 minutes before dividing into 3 pieces each of about 15 g. Subsequently, the doughs were proofed for 30 minutes at 25° C. and 80–85% RH, followed by moulding and shaping and placed in pans before proofing for 2 hours and 30 minutes at 25° C. and 80–85% RH. Two of the thus proofed dough pieces were baked at 250° C. for 7 minutes to provide loaves, and the third dough piece was frozen immediately for subsequent biochemical analysis.

The stickiness of the dough was evaluated after 40 minutes after addition of the enzyme solution and the increase in specific bread volume was calculated as the increase in volume in percentage compared to the volume of a loaf prepared from the dough without enzyme solution added.

The results of the experiment are summarized in table 4.1 below.

TABLE 4.1

Improvement of specific volumes of loaves prepared from Thesee flour dough supplemented with galactose oxidase (Units per kg flour) and Pectolytic enzyme 2524-70 (P70) (µl per kg flour)

| Enzyme solution | Specific volume increase (%) | Stickiness |
|---|---|---|
| Galactose oxidase, 150 U | 0 | |
| P70, 250 µl | 16 | +++ |
| P70, 250 µl + Galactose oxidase, 150 U | 18 | |
| P70, 250 µl + Galactose oxidase, 225 U | 16 | |
| P70, 250 µl + Galactose oxidase, 113 U | 17 | ++ |
| P70, 375 µl + Galactose oxidase, 225 U | 18 | |
| P70, 125 µl + Galactose oxidase, 75 U | 14 | + |
| P70, 375 µl + Galactose oxidase, 338 U | 21 | + |

The addition of galactose oxidase (150 U/kg) alone had no effect on the increase of the specific volume or the quality of the bread. Addition of P70 (250 µl/kg) alone did result in an increase of the specific volume, however, this was followed by a decrease in the dough quality as the dough was found very sticky.

It is evident from the above table that the addition of galactose oxidase and P70 had an increasing effect on the specific volume as compared to bread baked without addition of enzymes. The largest increase in specific volume was found with the addition of 375 µl P70 per kg flour and 338 U galactose oxidase per kg flour. However, this increase was followed by a decrease in dough quality as the dough was found to be sticky. The best results with regard to both specific volume and quality of the dough were obtained with the addition of 250 µl/kg P70 and 150 U/kg galactose oxidase.

4.2. The Effect of P70 and Galactose Oxidase on Different Types of Flour.

Using the method described the effect on the specific volume and stickiness of P70 (250 µl/kg flour) and galactose oxidase (150 U/kg flour) was tested during 8 different flours. The results are shown in table 4.2 below.

TABLE 4.2

Improvement of specific volumes of loaves prepared from flour doughs supplemented with galactose oxidase (150 U/kg flour) and Pectolytic enzyme 2524-70 (P70) (250 µl/kg flour)

| Flour | Specific volume increase (%) | Stickiness |
|---|---|---|
| Thesee | 18 | |
| Camp Remi | 15 | |
| Paris | 12 | |
| Soisson | 10 | |
| Arminda | 9 | |
| Annecy | 9 | |
| Tremie | 8 | + |
| Or | 6 | |

From these results, it is evident that the applied dosages of P70 and galactose oxidase resulted in an increase of the specific volume for all of the tested types flour. All doughs were found to be non-sticky except the dough prepared from Tremie flour. However, the control dough prepared from Tremie flour without enzymes added was also found to be sticky.

4.3. The Effect of Aarabinofuranosidase on the Specific Volume and the Quality of Bread Prepared from Thesee Flour.

It has been shown in Example 1 that arabinofuranosidase acting on arabinogalactan is capable of producing substrate for galactose oxidase. Doughs were prepared as described above and different combinations of the enzymes galactose oxidase, Grindamyl S 100 (Danisco Ingredients) and arabinofuranosidase were added hereto, see Table 4.3 and the effect on the specific volume and stickiness was determined. As a control was used dough made from Thesee flour and to which was added glucose oxidase and Grindamyl S 100.

Results are shown in Table 4.3 below.

TABLE 4.3

The effect on specific volumes and dough quality of bread prepared from thesee flour doughs supplemented with galactose oxidase (U/kg flour). Grindamyl S 100 (ppm) and arabinofuranosidase (U/kg flour)

| Enzymes | | | Specific volume increase (%) | Stickiness |
|---|---|---|---|---|
| Grindamyl S 100 | 500 | ppm | 19 | ++++ |
| Arabinofuranosidase | 30 | U | 0 | |
| Grindamyl S 100 | 500 | ppm | 19 | ++ |
| Arabinofuranosidase | 30 | U | | |
| Galactose oxidase | 150 | U | | |
| Grindamyl S 100 | 500 | ppm | 18 | +++ |
| Arabinofuranosidase | 100 | U | | |
| Galactose oxidase | 150 | U | | |
| Grindamyl S 100 | 500 | ppm | 20 | + |
| Galactose oxidase | 150 | U | | |
| Grindamyl S 100 | 500 | ppm | 22 | ++ |
| Glucose oxidase | 100 | ppm | | |

Grindamyl S 100 is known to result in an increase of the specific volume of the bread when applied to the dough. As the above results show this enzyme has the negative side effect of producing extremely sticky doughs. As can be seen from the above results, this side effect can be reduced significantly by the addition of galactose oxidase. The addition of arabinofuranosidase did not reduce the stickiness of the dough.

The increase in specific volume observed with the addition of grindamyl S 100 (500 ppm) and galactose oxidase (150 U/kg flour) is equivalent to that obtained with the addition of grindamyl S 100 (500 ppm) and glucose oxidase (100 ppm) however, the doughs containing galactose oxidase were found to be less sticky.

What is claimed is:

1. A flour dough improving composition comprising, as a first component a galactose oxidase as a second component: (a) at least one of a galactan, a galactose oligomer or a galactose dimer, (b) a galactose oligomer, and a galactanase, or (c) galactanase; and as a third component, flour.

2. A composition according to claim 1 wherein the galactose oxidase is derived from an organism which is selected from the group consisting of a plant species, a fungal species and a bacterial species.

3. A composition according to claim 1 which further comprises a cellulase, a starch degrading enzyme, a lipase or a protease.

4. A composition according to claims 1 or 3 further comprising a non-enzymic dough additive compound.

5. A composition according to claim 1 wherein the amount of the galactose oxidase is in the range of 1 to 10,000 units per g.

6. A method of preparing a flour dough comprising adding to the dough an amount of the composition of claim 1 which is sufficient to obtain an amount of galactose oxidase activity in the dough which is in the range of 1 to 10,000 units per kg of flour.

7. A method according to claim 6 wherein the flour dough is a noodle dough.

8. A method according to claim 7 wherein the flour dough is an alimentary paste dough.

9. A method of preparing a bakery product, comprising baking the flour dough obtained by the method of claim 6 with the composition of claim 1.

10. A method of preparing a dough product comprising adding the composition of claim 1 to dough ingredients, dough additives, a dough or a combination thereof.

11. A method according to claim 10, wherein the composition further comprises a cellulase, a starch degrading enzyme, a lipase or a protease.

12. A method according to claim 10 or 11, wherein the composition further comprises a non-enzymic dough additive compound.

13. A method according to claim 10 or 11, wherein the galactose oxidase in the composition added to the dough ingredients, dough additives or the dough is substantially free of other enzyme activities.

14. A method according to claim 10, wherein the galactose oxidase is in the form of a crude enzyme preparation.

15. The composition according to claim 1, wherein the second component is a galactan.

16. The composition according to claim 1, wherein the second component is a galactose oligomer.

17. The composition according to claim 1, wherein the second component is a galactose dimer.

18. The composition according to claim 1, wherein the second component is a galactose oligomer and a galactanase.

19. The composition according to claim 1, wherein the second component is galactanase.

* * * * *

UNITED STATES PATENT AND TRADEMARK OFFICE
CERTIFICATE OF CORRECTION

PATENT NO. : 6,929,936 B1
DATED : August 16, 2005
INVENTOR(S) : Xavier Rouau et al.

It is certified that error appears in the above-identified patent and that said Letters Patent is hereby corrected as shown below:

Column 15,
Line 42, insert -- and, -- after "galactose oxidase" and before "as a second component:".

Column 16,
Line 20, delete "with the composition of claim 1".

Signed and Sealed this

Thirty-first Day of January, 2006

JON W. DUDAS
*Director of the United States Patent and Trademark Office*